United States Patent [19]
Hornburg et al.

[11] Patent Number: 5,180,303
[45] Date of Patent: Jan. 19, 1993

[54] RETRIEVABLE DENTAL PROTHESIS APPARATUS AND METHOD OF FABRICATION

[75] Inventors: Wynn E. Hornburg, Stanton; John Beumer, III, Los Angeles, both of Calif.

[73] Assignee: Regents of the University of California, Oakland, Calif. ; by said John Beumer, III

[21] Appl. No.: 749,494

[22] Filed: Aug. 15, 1991

Related U.S. Application Data

[63] Continuation of Ser. No. 247,298, Sep. 21, 1988, abandoned.

[51] Int. Cl.$^5$ .............................................. A61C 8/00
[52] U.S. Cl. ................................... 433/173; 433/174
[58] Field of Search ............. 433/167, 169, 172, 173, 433/174, 175, 176, 206, 214, 213, 165, 166; 249/54; 264/19; 408/72 B, 85; 29/160.6; 164/34, 35, DIG. 4

[56] References Cited

U.S. PATENT DOCUMENTS

| | | | |
|---|---|---|---|
| 4,744,756 | 5/1988 | Ross | 433/173 |
| 4,758,161 | 7/1988 | Niznick | 433/173 |
| 4,793,808 | 12/1988 | Kirsch | 433/173 |
| 4,854,872 | 8/1989 | Detsch | 433/173 |

FOREIGN PATENT DOCUMENTS

2176709  1/1987  United Kingdom ............... 433/174

OTHER PUBLICATIONS

Booklet of Nobelpharma with copyright dated 1985.
Brochure of Interpore International dated May 1986.
Brochure of Core Vent Corporation for Symposium held Jun. 5-7, 1987.

*Primary Examiner*—Cary E. O'Connor
*Attorney, Agent, or Firm*—Poms, Smith, Lande & Rose

[57] ABSTRACT

A retrievable dental prothesis fabricated by using a special plastic cylinder using low-wax casting procedures for the purpose of eliminating the need for a visible titanium abutment cylinder typically used for conventional prostheses. This improves the appearance and functional features of the prosthesis. The prosthesis is connected by a titanium alloy screw directly to an implant embedded in a patient's underlying dental bone structure. Internal hexagonal surfaces formed at the base of the prosthesis which mate with hexagonal surfaces of an upward extension of the implant prevent loosening or rotation of the prosthesis due to rotational forces and vibrations and enable fabrication of single implant-supported restoration. However, the prosthesis may be used without such internal hexagonal surfaces if desired. Because an abutment cylinder is not used, the prosthesis provides increased working space between the implant and corresponding opposite upper or lower existing teeth. An access aperture may be provided at the back of the prosthesis for allowing access by an installation tool to the titanium alloy screw. The prosthesis is formed by shaping a wax pattern around the plastic cylinder to represent a patient's tooth to be replaced by the prosthesis. The prosthesis is then cast out of gold-palladium alloy. A bottom surface at the base of the prosthesis is polished using a lapping tool and guide pin. Cutting edges may be used on the lapping tool to facilitate deburring of the bottom surface.

37 Claims, 10 Drawing Sheets

RETRIEVABLE DENTAL PROTHESIS APPARATUS AND METHOD OF FABRICATION

This is a continuation of copending application Ser. No. 07/247,298 filed on Sep. 21, 1988, now abandoned.

BACKGROUND OF THE INVENTION

The present invention relates generally to dental prosthesis and, more particularly, to a retrievable dental prosthesis fabricated by using a special plastic cylinder during lost-wax casting procedures for the purpose of eliminating the need for a visible titanium abutment cylinder typically used for a conventional prosthesis in order to improve the appearance and functional features of the prosthesis.

In the past, the development of osseointegrated implants has allowed dental restorations or prostheses to be used with conventional titanium implants placed in a patient's bone structure underlying missing teeth for the purpose of replacing the lost teeth. Osseointegration (or bonding between the bone and implant) occurs so that the implant functions as a secure base on which to support a prosthesis. A conventional titanium (transmucosal) abutment cylinder is connected to the implant. The abutment is typically cemented to the implant or attached to it by a screw. As such, the abutment cylinder emerges from a patient's soft tissue (gum) and provides a structure upon which to mount the prosthesis. A prosthesis shaped like a tooth usually having a conventional cylinder incorporated into it is typically connected to the abutment cylinder by a screw.

Some problems have resulted in the past when a conventional titanium abutment cylinder has been used. For example, the titanium abutment cylinder extends from a patient's gum tissue (from the gingival crest) presenting an undesirable appearance due to the visible metallic cylinder. Also, inadequate interocclusal space between the abutment cylinder and opposing dentition may result in insufficient space for a conventionally designed prosthesis. Even when the shortest titanium abutment cylinder (3 mm) is used, the conventional cylinder incorporated within the prosthesis may be too large for the available working space. The heights of the conventional cylinder and the head of the cylinder screw may be decreased to accommodate the reduced working space, but this may compromise the integrity of the prosthesis.

A conventional prosthesis typically uses a titanium abutment cylinder that is either cemented to an implant or secured to it by a screw. Rotation of the abutment cylinder with respect to the implant is prevented by cementing the two parts together or using male and female mating surfaces (e.g., hexagonal extension from implant mating with internal hexagonal surfaces in abutment cylinder). However, the conventional cylinder is not cemented to the abutment cylinder, nor do these two parts have mating male and female surfaces that prevent rotation of the parts. A screw holds the conventional cylinder to the titanium abutment cylinder.

Loosening and rotation of the conventional and titanium abutment cylinders with respect to each other will take place when the cylinders experience sufficient rotational forces and vibration. Rotation and loosening would be less likely if the prosthesis is anchored to another prosthesis, or a natural tooth (or adjacent teeth). However, prostheses using such anchoring means to prevent loosening and rotation thereof are more expensive and less attractive in appearance than a prosthesis not using such anchoring means.

Another disadvantage of some conventional prostheses relates to the difficulty in treating infections or other dental problems that may develop in those dental cases where the titanium abutment cylinder is cemented to the implant. In such cases, surgery may be required to remove the cemented parts in order to treat the problem areas.

Many of these problems would be eliminated or improved by providing a prosthesis directly connected at its base to an implant that may be easily removed from the implant and that uses mating male and female surfaces to prevent rotation. The prior art does not disclose or suggest such a prosthesis, which would eliminate the need for an unsightly titanium abutment cylinder, provide increased working space between the implant and a corresponding upper or lower tooth due to elimination of the abutment cylinder, prevent rotation of the prosthesis with respect to the implant, and allow removal of the prosthesis for maintenance, oral hygiene, or when infections occur.

In addition, proper dental hygiene may be difficult when a titanium abutment cylinder is used because the titanium abutment cylinder may not provide appropriate hygiene access or desirable contours near soft tissue areas adjacent the cylinder required for oral hygiene and a healthy gingival response. Also, plaque tends to accumulate more readily on a machined metal surface, such as a titanium abutment cylinder, than on, for example, a polished porcelain surface.

SUMMARY OF THE INVENTION

Many of the above-mentioned problems would be lessened by providing a prosthesis that is directly connected to its dental implant without the need for an abutment cylinder. Such a prosthesis could be desirably contoured at its base and given a porcelain surface that would improve appearance and access for dental hygiene. The prior art does not disclose or suggest such a desirable prosthesis design.

Simply decreasing the number of parts needed for a conventional prosthesis by eliminating the need for a titanium abutment cylinder, would simplify a prosthesis design improving aesthetics and appearance. Moreover, connecting the prosthesis directly to the implant eliminates the need for a close tolerance fit between the conventional cylinder and titanium abutment cylinder typically used for a conventional prosthesis. A close tolerance fit would be required between the prosthesis base and the implant to prevent bacteria or substances from entering the interface between the base and implant.

Problems have resulted in the past if an implant is improperly placed or aligned in a patient's bone structure. It is often necessary to gain access to the screw holding the abutment cylinder to the implant through the front of the prosthesis attached to the abutment cylinder. As a result, an access aperture is sometimes made through the visible front portion of the prosthesis that must be filled using cosmetic dental procedures in order to present an attractive appearance, leading to a more time consuming and expensive dental procedure. Therefore, there is a need to develop a prosthesis removably secured to an implant (which may be aligned at an inconvenient angle) that would allow access to a screw holding the prosthesis to the implant through an access aperture from behind the prosthesis. As such, unnecessary cosmetic dental expenses would be eliminated because the access hole may be filled at the nonvisible back portion of the prosthesis eliminating the need for costly cosmetic dental work.

It would also be advantageous to provide an economical method of fabricating a retrievable dental prosthesis attached directly to an implant as described above. In addition, new tooling or apparatus are needed for manufacturing such a prosthesis.

Accordingly, there is a need for a retrievable dental prosthesis secured directly to an implant that eliminates the need for an unsightly visible titanium abutment cylinder typically used for a conventional prosthesis, eliminates rotation of the prosthesis with respect to the implant by using mating male and female surfaces, allows for easy removal of the prosthesis from the implant for maintenance, oral hygiene, or when infections occur, provides desirable prosthesis contours near soft tissue areas and a close tolerance fit between the base of the prosthesis and the implant, and allows easy access from the rear of the prosthesis to a screw securing the prosthesis to the implant. There is also a need for an economical method used for fabricating such a removable dental prosthesis, and for tooling or apparatus used in connection with such fabrication.

It is an object of this invention to provide a retrievable dental prosthesis that may be secured easily and directly to a dental implant without using a titanium abutment cylinder in order to improve the appearance of the prosthesis and allow the prosthesis to be removed from the implant for maintenance, oral hygiene, or other purposes.

It is still another object of the invention to provide a retrievable dental prosthesis that presents increased working space between the implant it is connected to and opposing dentition by eliminating the need for a titanium abutment cylinder.

It is still another object of this invention to provide a retrievable dental prosthesis that will not rotate with respect to the implant it is connected to, thus, eliminating the need to anchor the prosthesis to adjacent teeth or other prostheses.

It is still another object of this invention to provide a retrievable dental prosthesis that overcomes positional and angulation problems associated with implants embedded in a patient's bone structure.

It is still another object of this invention to provide a retrievable dental prosthesis that has a close tolerance fit between the base of the prosthesis and an implant.

It is still another object of this invention to provide a retrievable dental prosthesis that has desirable contours near soft tissue areas in order to improve soft tissue health and hygiene access.

It is still another object of this invention to provide an economical method for fabricating a retrievable dental prosthesis connected directly to an implant without using a titanium abutment cylinder, and to provide tooling or apparatus for such fabrication.

These and other objects and advantages are attained by a retrievable dental prosthesis fabricated by using a special plastic cylinder using lost-wax casting procedures for the purpose of eliminating the need for a visible titanium abutment cylinder typically used for conventional prostheses. This results in improved appearance and functional features of the prosthesis. The prosthesis is connected by a titanium alloy screw directly to an implant embedded in a patient's underlying dental bone structure. Internal hexagonal surfaces formed at the base of the prosthesis which mate with hexagonal surfaces of an upward extension of the implant prevent loosening or rotation of the prosthesis due to rotational forces and vibrations and enable fabrication of single implant-supported restoration. Because an abutment cylinder is not used, the prosthesis provides increased working space between the implant and corresponding opposite upper or lower existing teeth.

An access aperture may be provided at the back of the prosthesis for allowing access by an installation tool to the titanium alloy screw securing the prosthesis to the implant in order to loosen or tighten the screw for installation, maintenance, or oral hygiene purposes. The screw has internal hexagonal surfaces in its head forming a recess which facilitates engagement by the installation tool. Such a recess is known as an Allen head recess in the machine tool field. A titanium alloy screw having a slotted head rather than a head with internal hexagonal surfaces may be used for a prosthesis which does not present access problems when tightening and loosening the titanium alloy screw.

The retrievable dental prosthesis is fabricated by first placing an implant in a working cast so that the hexagonal surfaces of the implant are oriented correctly. A plastic cylinder is then mounted on the implant. A top portion of the cylinder is then cut off so that the cylinder matches the heights of adjacent teeth. A wax pattern is then formed around the plastic cylinder to conform to the contours of a patient's missing tooth to be replaced by the prosthesis. Additional wax may be used to form internal hexagonal surfaces at the base of the cylinder. The internal hexagonal surfaces may be omitted from the base of the cylinder, if desired. The wax pattern and cylinder are then placed in a mold and gold-palladium alloy is used to cast a metal prosthesis using lost-wax casting procedures. The plastic cylinder is shaped so that a collar is provided around the base of the cast metal prosthesis in order to strengthen the prosthesis.

A bottom surface at the base of the prosthesis is polished using a lapping tool and guide pin. Cutting edges may be used on the lapping tool to facilitate deburring or polishing of the bottom surface. A porcelain layer may be fused to the cast metal alloy prosthesis. The porcelain layer extends down to the collar at the base of the prosthesis providing desirable contours for soft tissue areas adjacent the base of the prosthesis to facilitate soft tissue health and provide access for oral hygiene purposes.

The various features of the present invention will be best understood together with further objects and advantages by reference to the following description of the preferred embodiments taken in conjunction with the accompanying drawings.

DESCRIPTION OF THE PREFERRED EMBODIMENTS

The following specification taken in conjunction with the drawings sets forth the preferred embodiments of the present invention in such a manner that any person skilled in the art can make and use the invention. The embodiments of the invention disclosed herein are the best modes contemplated by the inventors for carrying out their invention in a commercial environment although it should be understood that various modifications can be accomplished within the parameters of the present invention.

Figures 1, 2:
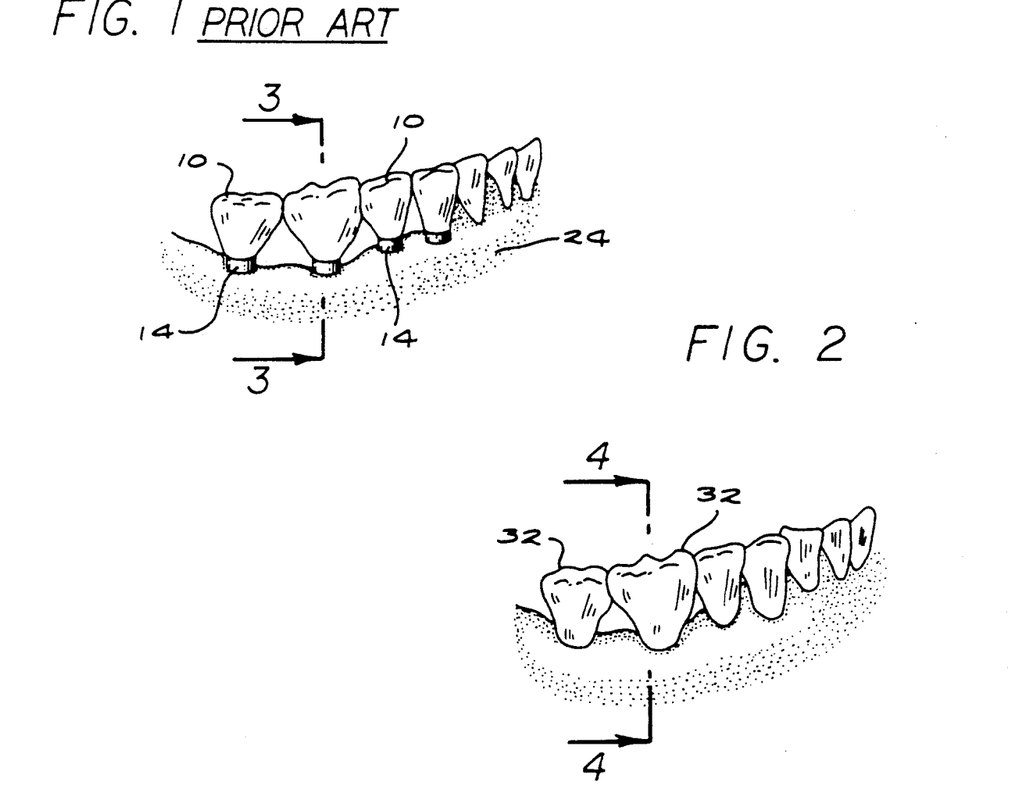
FIG. 1 is a perspective view of conventional dental prostheses showing the prostheses attached to titanium abutment cylinders extending up from the gingiva (gum) of a patient.
FIG. 2 is a perspective view of a plurality of retrievable dental prostheses mounted in a patient's mouth illustrating the principles of the present invention and showing the improved appearance of the prostheses obtained by eliminating the use of a titanium abutment cylinder.
Figure 3:
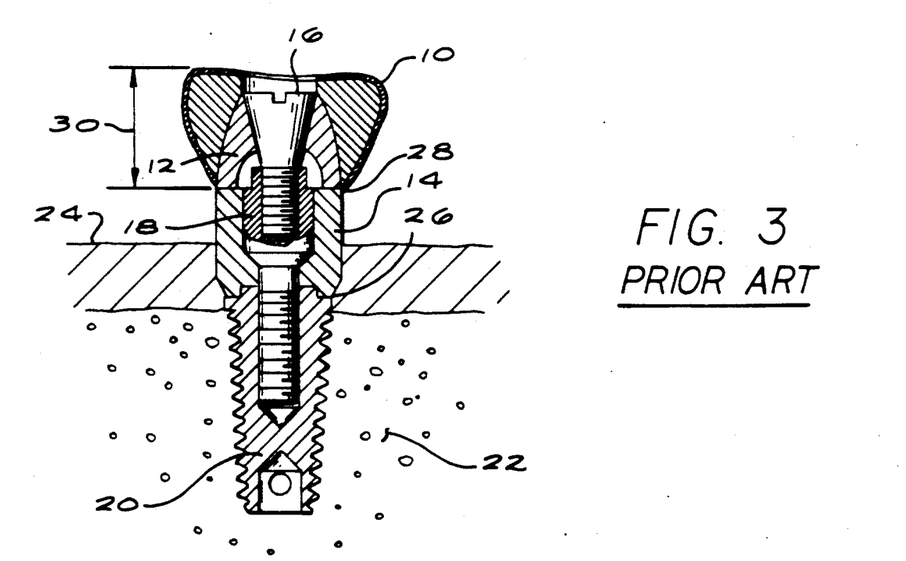
FIG. 3 is a partial cross-sectional view of one of the prostheses and titanium abutment cylinders of FIG. 1 and of an implant taken in the direction of arrows 3—3 of FIG. 1 showing how the prosthesis is attached to the abutment cylinder by a screw and the cylinder is secured by another screw to the implant placed in a patient's bone structure.

FIGS. 1 and 3 illustrate a conventional dental prosthesis 10. A cylinder 12 incorporated into the prosthesis 10 is attached to a titanium abutment cylinder 14 by a screw 16. Cylinder 12 may be a gold-palladium cylinder and screw 16 may be a gold alloy screw. The titanium abutment cylinder 14 extends through the tissue or gums 24 of a patient and is, thus, termed a "transmucosal" abutment cylinder 14. The titanium abutment cylinder 14, in turn, is secured by another screw 18 to an implant 20 placed into the bone structure 22 of a patient. The titanium abutment cylinder 14 emerges from the gums 24 of the patient presenting an unsightly appearance as shown in FIG. 1. The abutment cylinder 14 is prevented from rotating with respect to the implant 20 by male and female hexagonal surfaces existing at interface 26. Alternatively, the abutment cylinder 14 may be cemented to the implant 20 eliminating the need for a screw 18. However, the cylinder 12 is not prevented from rotating with respect to the abutment cylinder 14 by hexagonal surfaces, or any other securing arrangements, at interface 28 and may loosen and rotate if sufficient rotational forces or vibrations are present. This results in undesirable loosening of the prosthesis 10 as a result of chewing forces applied to the prosthesis 10. To prevent such rotation, conventional prostheses have been anchored to adjacent teeth or to other prostheses which may result in increased expenses and may lead to an unnatural or unattractive appearance.

Due to the height of the titanium abutment cylinder 14, inadequate working or interocclusal space 30 may exist between the top of the abutment cylinder 14 and a corresponding upper or lower tooth or occlusal level (not shown) opposite the cylinder 14. The cylinder 12 may be too large even when the shortest titanium abutment cylinder 14 is used leading to insufficient working space 30 for the prosthesis 10. In addition, the titanium abutment cylinder 14 may not provide adequate access or desirable contours near soft tissue areas adjacent the cylinder 14 required for oral hygiene and a healthy gingival response. Incidentally, the term "gingiva" means gum, and "gingival" is the related adjective.

Figures 4, 5:
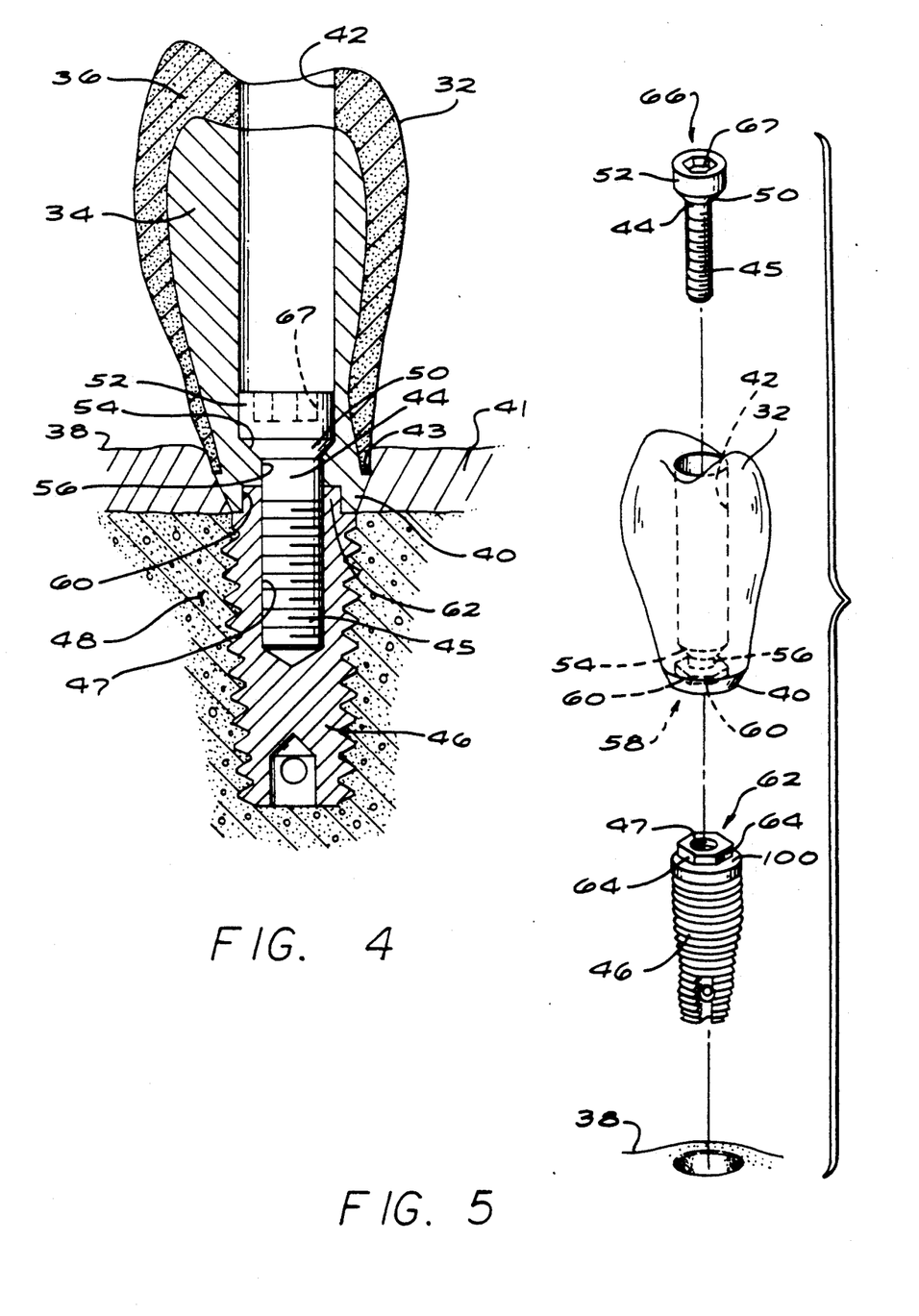
FIG. 4 is a partial cross-sectional view of one of the retrievable dental prostheses of FIG. 2 and an implant taken in the direction of arrows 4—4 of FIG. 2 showing how the integral and unitary prosthesis is directly connected by a titanium alloy screw to the implant placed in a patient's bone structure.
FIG. 5 is an exploded perspective view of the retrievable dental prosthesis, screw and implant of FIG. 4.

FIGS. 2, 4, and 5 show a preferred embodiment of the removable dental prosthesis 32 of the present invention. The prosthesis 32 is made out of cast metal 34 as will be explained later. The cast metal 34 is preferably a 51 percent gold-palladium alloy. However, any desirable crown and bridge dental alloy, or the like, may be used. It is not intended that the present invention be limited to any particular group of metals that may be used for the cast metal 34 and, therefore, any type of desirable cast metal may be used. A layer of porcelain 36 may be fused to the cast metal 34 in order to present an attractive appearance, minimize plaque buildup, etc. The cast metal 34 and porcelain layer 36 extend below the upper surface 38 of the soft tissue 41 as shown in FIG. 4 in order to present an attractive appearance for the prosthesis 32 and to provide adequate access or desirable contours near soft tissue around the bottom of the prosthesis 32, needed for oral hygiene (flossing, growth of tissue around bottom of prosthesis helping to prevent gaps between tissue and prosthesis, etc.) and soft tissue health.

The prosthesis 32 has an annular shoulder or collar 40 at its base to provide increased structural strength and an annular ledge 43. The porcelain layer 36 extends down to the ledge 43 as best shown in FIG. 4. A cylindrically-shaped bore 42 passes from the top to the bottom of the prosthesis 32 providing access to a titanium alloy screw 44 which attaches the prosthesis 32 to an implant anchor 46 placed in the bone structure 48 of a patient. "Implant anchor" was used herein means an implant 46 as shown in FIG. 4, and cylinder 14 shown in FIG. 3, or any other separate part between the anchor and prosthesis, is not considered part of the implant anchor. The screw 44 has a threaded end 45 which screws into internal threads 47 in the implant 46. The screw 44 may have a frustro-conically-shaped surface 50 at the bottom of its head 52 which bears against a matching frustro-conically-shaped internal surface 54 of the prosthesis 32. A smaller cylindrically-shaped bore 56 passes through the bottom of the prosthesis 32 into a recessed area 58 of the prosthesis 32 having internal hexagonal surfaces 60 (see FIGS. 5 and 6). The titanium alloy screw 44 passes through bore 56 and threads into the implant 46 holding the prosthesis 32 to the implant 46.

Figures 24, 26:
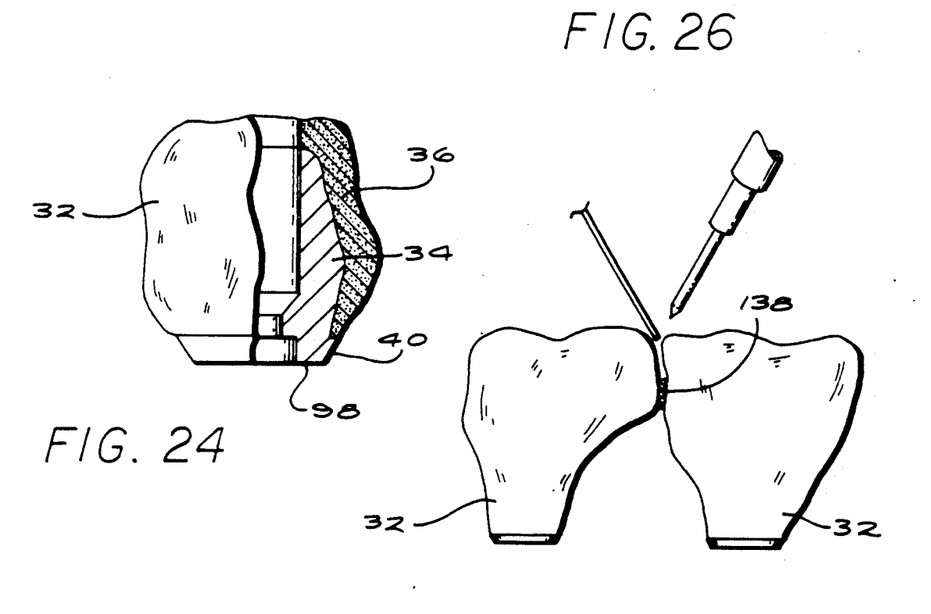
FIG. 24 is a partial cross-sectional view of the finished prosthesis of FIG. 23 after a porcelain layer has been fused to the outer surface of the cast metal prosthesis.
FIG. 26 is a perspective view of two of the prostheses of FIG. 4 showing how the two prostheses can be soldered together.

The implant 46 is preferably a titanium implant used as part of the components of an implant system sold under the trademark BRANEMARK SYSTEM by Nobel Pharma U.S., Inc., Waltham, Mass. However, other types of implants may be used with the prosthesis 32 and other screws may be used instead of the titanium alloy screw 44 such as gold alloy screws, or screws made out of other alloys. The implant 46 has an upward extension 62 with hexagonal surfaces 64 which engage and match the hexagonal surfaces 60 of the prosthesis 32 thereby preventing rotation of the prosthesis with respect to the implant 46. However, any type male and female mating or interlocking surfaces may be used instead of the hexagonal surfaces 60 and 64 in order to prevent rotation. Thus, the present invention provides an important advantage over the conventional prosthesis 10 of FIG. 3 because new prosthesis 32 will not loosen or rotate due to rotational forces or vibrations experienced by the prosthesis 32 as a result of chewing forces or the like. As such, the prosthesis 32 may be used for a simple implant-supported restoration. On the other hand, the prosthesis 32 may be used without hexagonal surfaces 60 which are not needed if the prosthesis 10 is attached to an adjacent tooth or prosthesis 10 such as illustrated in FIG. 26.

Figures 6, 7, 8, 9:
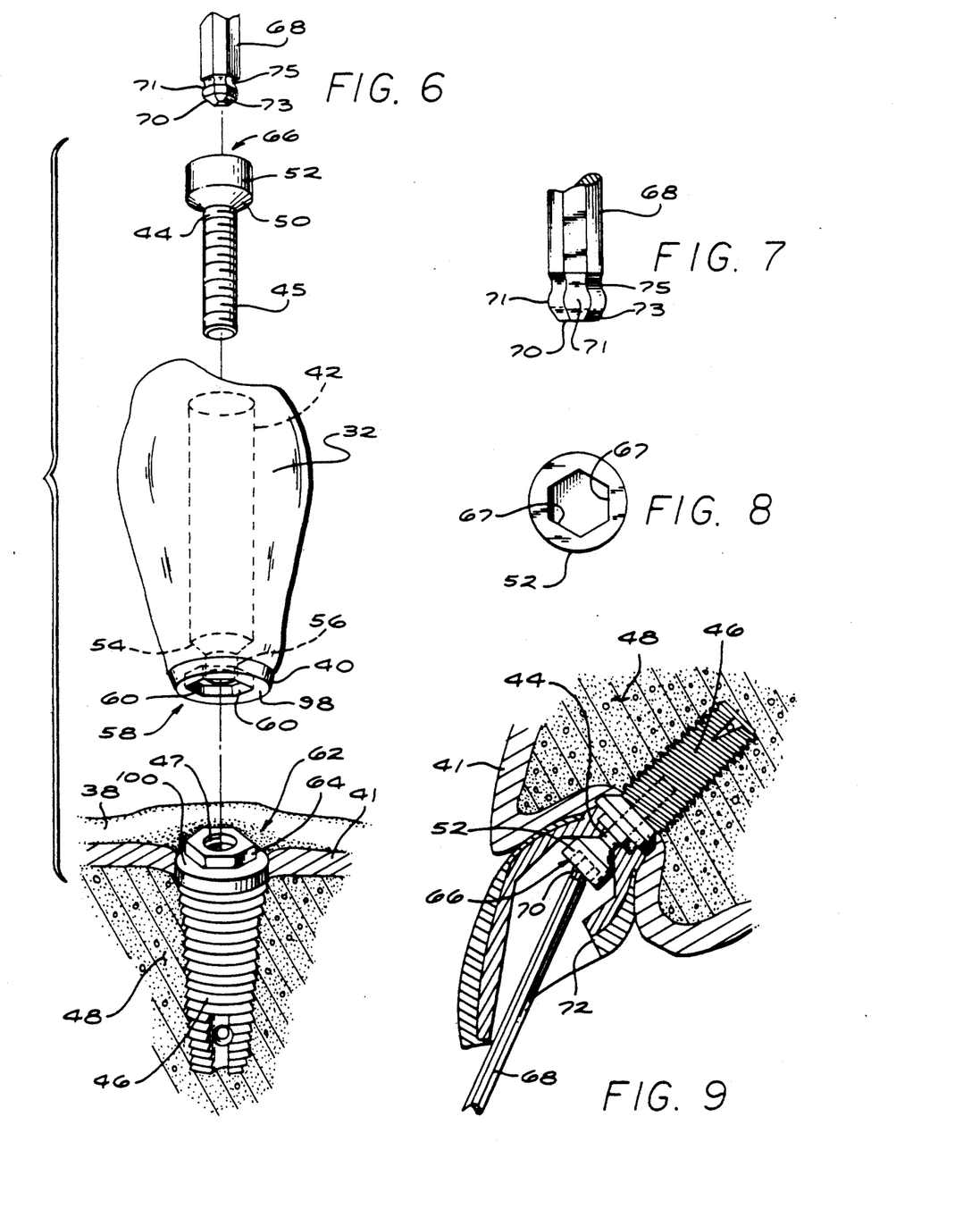
FIG. 6 is another exploded perspective view of the retrievable dental prosthesis, screw and implant of FIG. 4 showing how an installation tool may be used with the present invention.
FIG. 7 is an enlarged detailed view of an engaging end of the installation tool of FIG. 6.
FIG. 8 is an enlarged, detailed, top plan view of the head of the screw of FIG. 5.
FIG. 9 is a partial cross-sectional view of the retrievable dental prosthesis, screw and implant of FIG. 4 and the installation tool of FIG. 6 showing how access to the screw by the installation tool is obtained through an access aperture from the back of the prosthesis.

Referring now to FIGS. 5 through 8, an installation tool 68 is used to install the titanium alloy screw 44 which holds the prosthesis 32 to the implant 46. The installation tool 68 has an engaging end 70 with engagement surfaces 71 and 73 that are designed to operably engage a recess 66 in the head 52 of the screw 44 which preferably has internal hexagonal surfaces 67 forming a hexagonal recess 66. Such a hexagonal recess 66 is known in the machine tool field as an Allen head recess. Any desirable designs may be used for the engaging end 70 and recess 66 so long as end 70 is able to engage any desirable type of material surfaces in recess 66 at different angles and still be able to tighten and loosen the screw 44. It may be noted that the end 70 of the tool 68 as shown in FIG. 7 is recessed at area 75 to provide clearance when the tool 68 is not directly aligned with screw 44. Thus, when the tool 68 is at an angle, engagement surfaces 71 and 73 of the tool end 70 will still engage the recess 66 to apply rotational torque to the screw 44, with the recessed area 75 permitting sufficient entry of the end 70 of the tool 68 to maintain peripheral contact with recess 66.

FIG. 9 shows how the installation tool 68 may be used to access the titanium alloy screw 44 through an access aperture 72 from the back of the prosthesis 32. The installation tool 68 can be used to gain access to the screw 44 in cases where the implant 46 is aligned in such a way that access to the screw 44 for tightening and loosening the screw 44 for installation and maintenance would be difficult using conventional installation tools. If a conventional tool is used in such cases, access would probably be obtained through an access aperture through the front of a prosthesis requiring expensive time-consuming cosmetic dental work to fill in the access aperture after the prosthesis is installed. As such, the installation tool 68 when used with the recess 66 in the head 52 of the screw 44 provides important advantages over conventional installation tools, such as a standard Allen head wrench with a straight shank.

The installation tool 68 may be used to easily loosen screw 44 and disconnect or remove the prosthesis 32 from the implant 46 for maintenance, oral hygiene, etc. Therefore, the prosthesis 32 is "removable" or "retrievable" in the true sense of the word, and can be later secured back to the implant 46 using tool 68 and the access aperture 72 can be filled with resin using conventional techniques. As such, the prosthesis 32 is the only truly removable dental prosthesis that will not rotate due to rotational forces or vibrations even though the prosthesis 32 is not anchored to adjacent teeth or prostheses.

Figure 10:
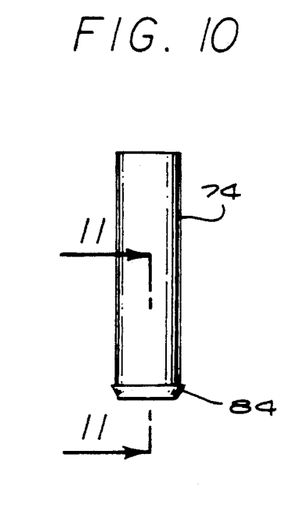
FIG. 10 is an elevational view of a plastic cylinder used to fabricate the retrievable dental prosthesis of FIG. 4.
Figure 11:
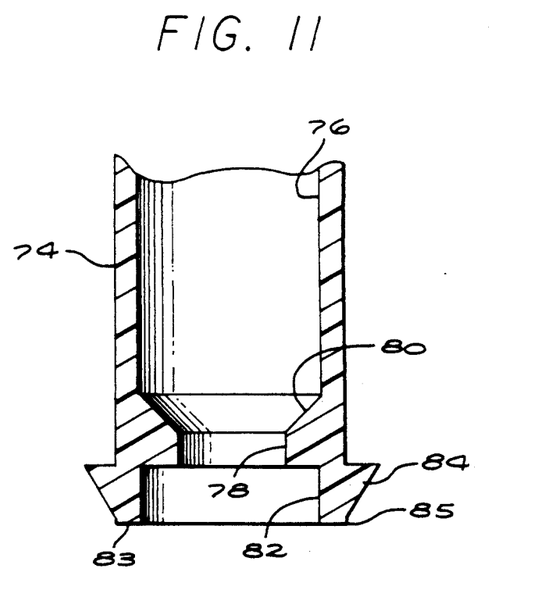
FIG. 11 is an enlarged detailed cross-sectional view of the base of the plastic cylinder of FIG. 10.

A plastic cylinder 74, shown in FIGS. 10 and 11, is used to fabricate the prosthesis 32. Preferably, the cylinder 74 is made out of a plastic material such as Delrin. However, any type of material may be used for the cylinder 74 that can be used for lost-wax casting procedures. The cylinder 74 has an internal bore 76, a smaller internal bore 78, a frustro-conically-shaped internal surface 80, and a cylindrically-shaped recess 82. There is a shoulder or collar 84 at the base of the cylinder 74 and a downwardly extending portion 85 and bottom surface 83 at the base. An annular ledge 81 exists at the top of collar 84. As will be explained later, bores 76 and 78 of the cylinder 74 are the same sizes as corresponding bores 42 and 56 of the prosthesis 32. In addition, surface 80 of the cylinder 74 is identical to corresponding surface 50 of the prosthesis 32, and corresponding cylindrically-shaped recesses 58 and 82 are also identical. Finally, collars 40 and 84, ledges 43 and 81, and portions 55 and 85 (see FIG. 18) have similar dimensions, and bottom surfaces 98 and 83 are identical.

Figures 12, 13:
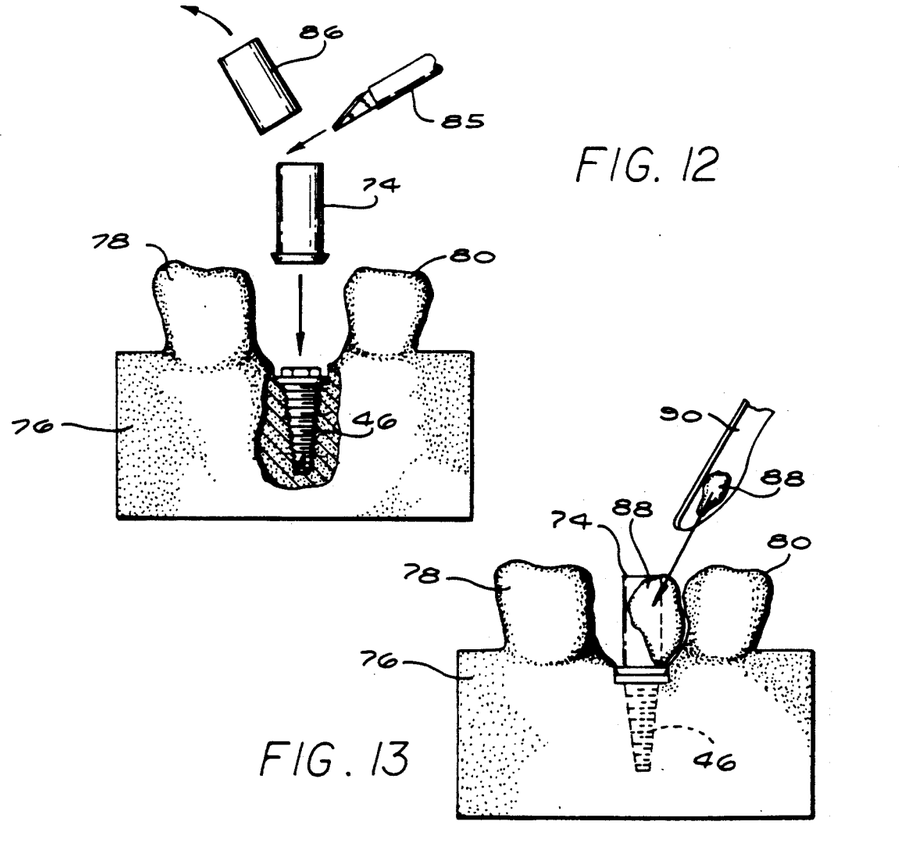
FIG. 12 is an elevational view of the plastic cylinder of FIG. 10 and of a lower master cast with a portion thereof broken away to show the implant of FIG. 4 placed in the cast illustrating certain aspects of the present invention and how the cylinder may be mounted on top of the implant and part of the cylinder may be cut off to match adjacent cast teeth.
FIG. 13 is an elevation view of the lower master cast, plastic cylinder and implant of FIG. 12 (indicating the implant by broken lines) showing how wax may be built up around the cylinder to achieve desired contours conforming to the contours of adjacent cast teeth.
Figure 14:
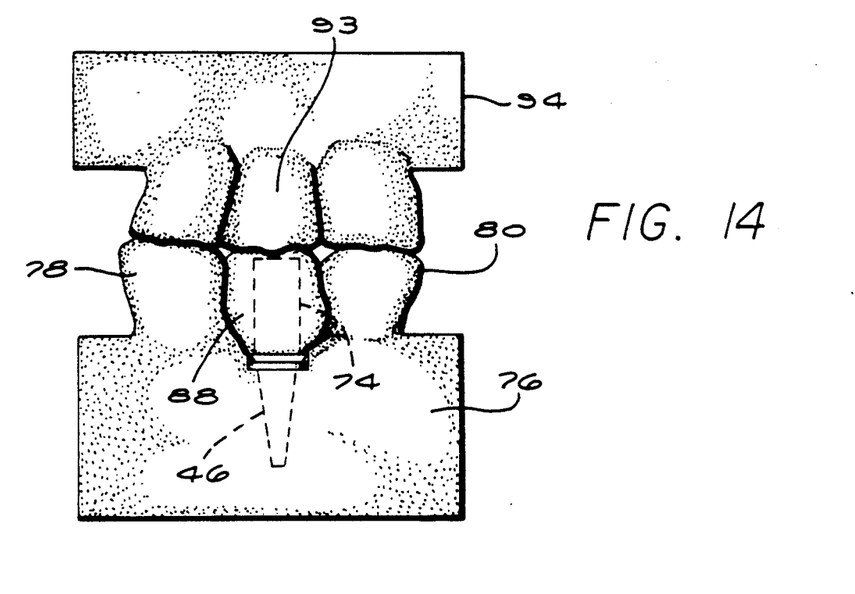
FIG. 14 is an elevational view of the lower master cast, plastic cylinder and implant of FIG. 13 (indicating the plastic cylinder and implant by broken lines) and of an upper master cast resting on top of the lower cast illustrating certain aspects of the present invention and showing how the wax is formed around the cylinder to achieve desired contours or a wax pattern of a tooth to match the contours of the cast teeth of both the upper and lower master casts.

FIGS. 12 through 14 show how the plastic cylinder 74 is used to fabricate the prosthesis 32. First, an implant analogue 46 is placed in a lower master cast 76 prepared to represent the teeth 78 and 80 of a patient and the missing tooth (not shown) to be replaced by the prosthesis 32. If a prosthesis 10 without hexagonal surfaces 60 is to be fabricated, then wax 88 is not built up in recess 88. It is important to note that the implant 46 must be positioned in the cast 76 so that the hexagonal surfaces 64 are properly oriented in the same positions they will be in when the implant 46 is placed in a patient's bone structure 48 so that the prosthesis 32 will be properly oriented when installed in the patient's mouth. The cylinder 74 is placed on top of the implant 46 and a top part or portion 86 of the cylinder 74 is then cut off by a cutting instrument 87 so that the height of the remaining portion of the cylinder 74 roughly matches the heights of adjacent teeth 78 and 80. Wax 88 is then shaped around the cylinder 74 by a shaping instrument 90 as shown in FIG. 13 so that the contours of the wax shaped surface 88 match contours of the adjacent teeth 78 and 80 and the contours of an upper tooth 93 contained in an upper master cast 94 as shown in FIG. 14. As such, wax 88 may be easily formed around the cylinder 74 to represent the shape or contours of the missing tooth (not shown) to be replaced by the prosthesis 32 or to form a wax pattern.

Figures 15, 16:
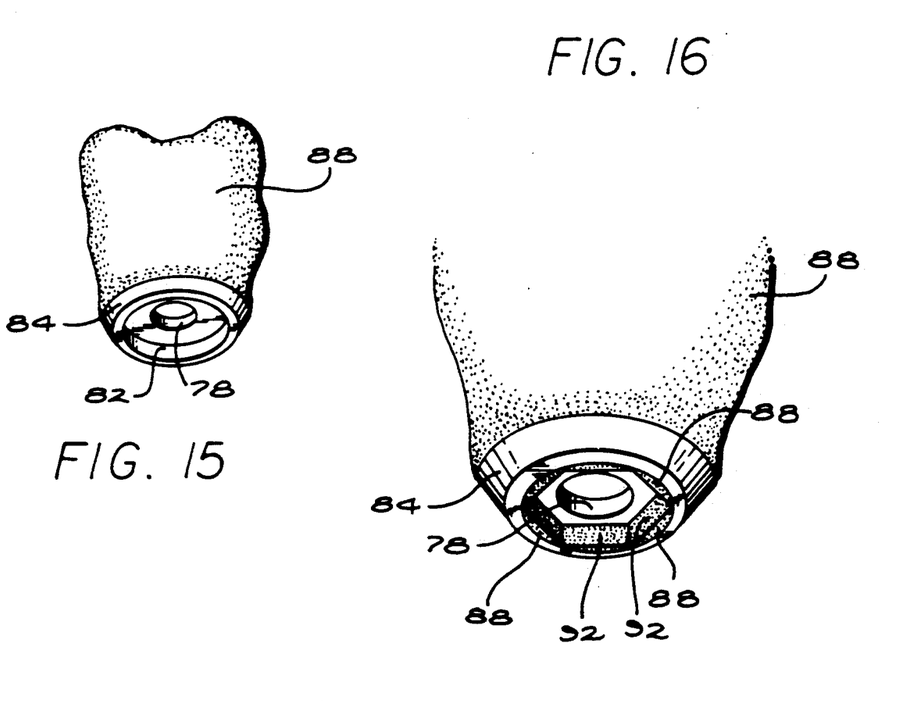
FIG. 15 is an enlarged, detailed perspective view of the base of the plastic cylinder of FIG. 14 after it has been removed from the lower master cast of FIG. 14.
FIG. 16 is an enlarged, detailed perspective view of the base of the plastic cylinder of FIG. 15 showing how wax may be built up in a cylindrically-shaped recess at the bottom of the cylinder to form internal hexagonal surfaces.

After the wax surface 88 has been formed around cylinder 74, the cylinder 74 with wax 88 is removed from the implant 46 or lower cast 76. FIG. 15 shows the base of the cylinder 74 after wax 88 has been shaped around it with the cylindrically shaped recess 82 visible at the base thereof. However, wax 88 may be built up in recess 82 to form internal hexagonal surfaces 92 at the base of the cylinder 74 before the cylinder 74 is initially placed on top of the implant 46 in the cast 76. Surfaces 92 are identical to surfaces 60 of the prosthesis 32. If a prosthesis 32 without hexagonal surfaces 60 is to be fabricated, then wax 88 is not built up in recess 88. It is important to note that cylinder 74 may have internal hexagonal surfaces similar to surfaces 92 internally formed, fabricated or machined at the base of the cylinder 74 eliminating the need to use wax 88 to form the hexagonal surfaces 92 at the base of the cylinder 74. Therefore, the present invention is intended to include a cylinder 74 having internal hexagonal surfaces 92 formed integrally at its base.

As previously mentioned, any type of male and female mating surfaces may be used instead of the hexagonal surfaces 60, 64 and 92 that will prevent the prosthesis 32 from rotating with respect to the implant 46. Similarly, surfaces other than hexagonal surfaces may be internally formed, fabricated or machined at the base of the cylinder 74.

Figure 17:
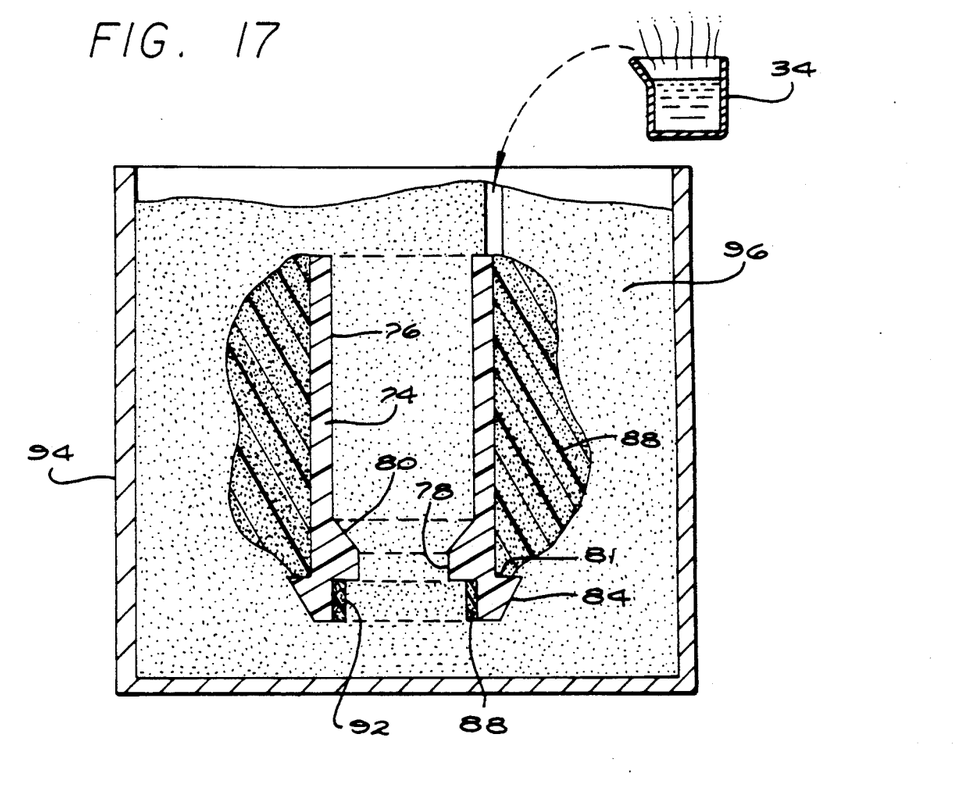
FIG. 17 is a schematic representation showing how molten metal is used to cast the prosthesis of FIG. 4 using lost-wax casting procedures.
Figure 18:
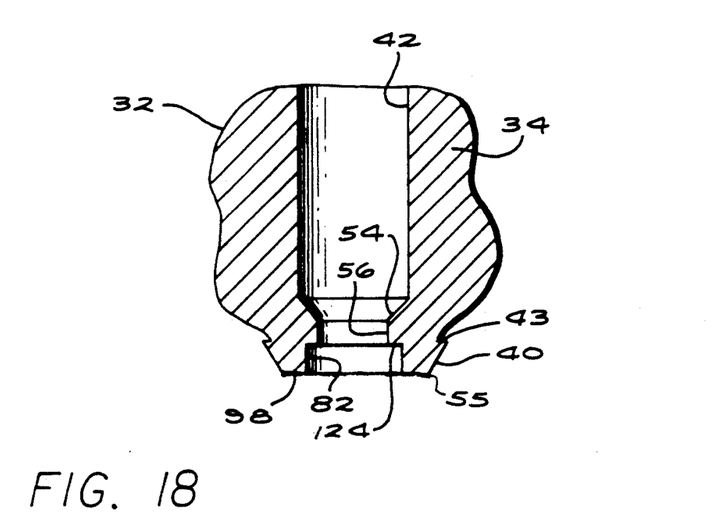
FIG. 18 is a cross-sectional view of a cast metal prosthesis fabricated using the lost-wax casting procedures of FIG. 17.

FIG. 17 schematically shows how the cylinder 74 with wax 88 built up around it to form a wax pattern or represent a missing tooth or prosthesis 32 is placed in a mold 94 which is filled with casting investment material 96 as shown. Using conventional methods, wax 88 and cylinder 74 are melted by and replaced by the molten casting material 34 using conventional lost-wax casting procedures to form a cast metal 34 prosthesis 32 as shown in FIG. 18 with collar 40, bores 42 and 56, frustro-conically-shaped surface 54 and downwardly extending portion 55. As previously discussed, the cast metal 34 is preferably 51 percent gold-palladium alloy. If internal hexagonal surfaces 60 are required, then these surfaces may be formed during the lost-wax casting procedure by wax-formed surfaces 92. If not, then the base of the prosthesis 32 will have a cylindrically-shaped recess 82 with bottom surface 124 as indicated in FIG. 18. Preferably, the prosthesis 32 has hexagonal surfaces 60 at its base to prevent loosening or rotation of the prosthesis as previously explained. However, the prosthesis 32 may be fabricated without the hexagonal surfaces 60 if desired.

Figure 19:
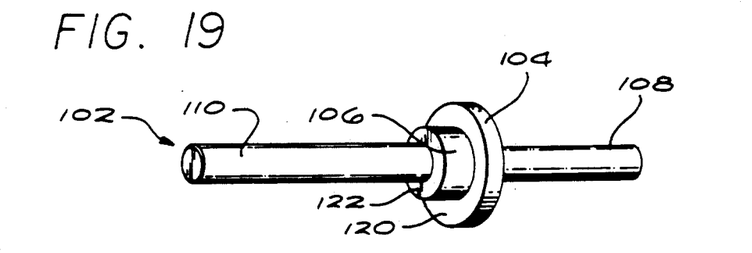
FIG. 19 is a perspective view of a lapping tool used to polish a bottom surface of the prosthesis of FIG. 4.
Figure 20:
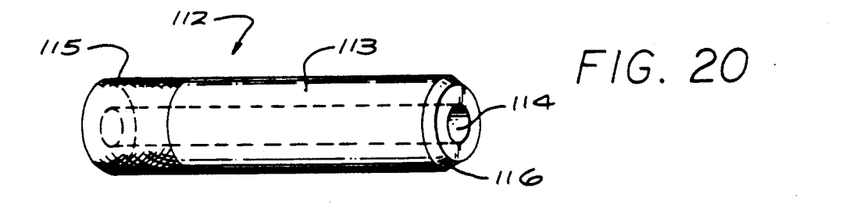
FIG. 20 is a perspective view of a guide pin used with the lapping tool of FIG. 19 to polish the bottom surface of the prosthesis of FIG. 4.

FIGS. 19 through 23 show how new milling tools illustrating the principles of the present invention are used to lap, deburr or polish a bottom surface 98 at the base of the prosthesis 32 so that the surface 98 fits closely with upper surface 100 of the implant 46 (see FIG. 5). It is important to have a tight and close tolerance fit between surfaces 98 and 100 to keep bacteria or substances from entering the interface between the base of the prosthesis 32 and the implant 46. A lapping tool 102 is shown in FIG. 19 having a deburring flange 104, shank 106, shaft 108, connectable to a source of torque, and engaging rod 110. The tool 102 is used with a guide pin 112 shown in FIG. 20. The guide pin 112 has an internal bore 114 passing longitudinally through the length thereof, a frustro-conically-shaped surface 116 that matches surface 50 of the prosthesis 32 and a gripping surface 115.

Figure 22:
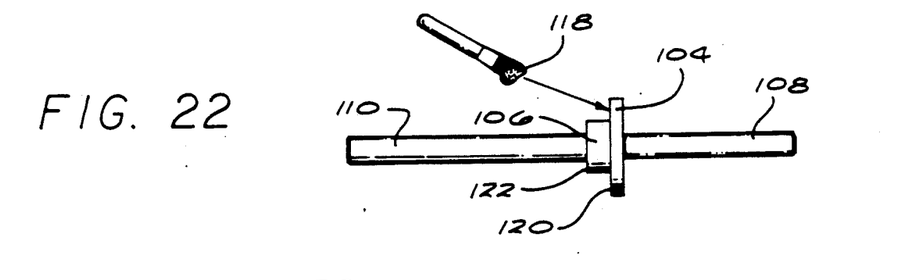
FIG. 22 is an elevational view of the lapping tool of FIG. 19 showing an abrasive paste being applied to a deburring flange of the tool.
Figure 23:
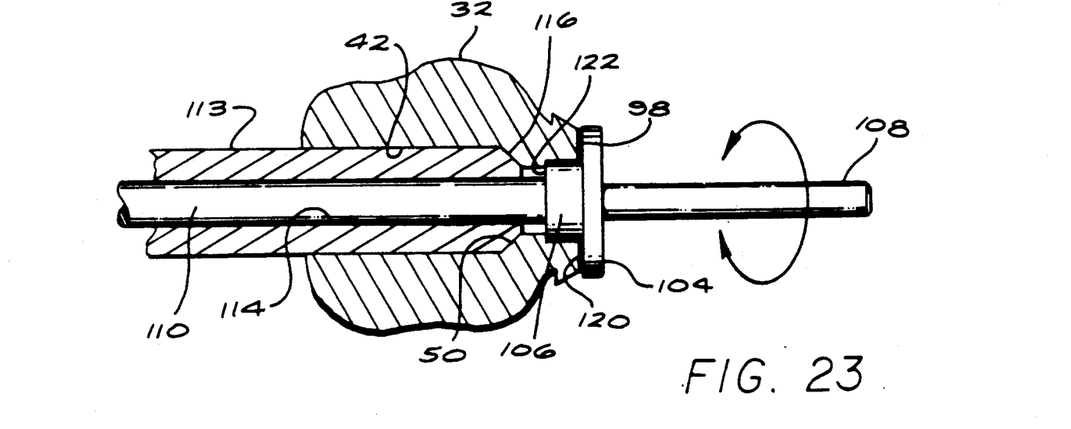
FIG. 23 is a partial cross-sectional view of the prosthesis of FIG. 4 mounted on the lapping tool of FIG. 19 and guide pin of FIG. 20 showing how the bottom surface of the prosthesis is polished.

Abrasive milling paste 118 such as diamond paste is brushed onto engaging surface 120 of the lapping tool 102. The lapping tool 102, with paste 118 on surface 120, is used with the guide pin 112 to polish bottom surface 98 of the prosthesis 32 as shown in FIG. 23. The guide pin 112 has an external cylindrical surface with a diameter 113 which is sized to allow the pin 112 to be inserted into bore 42 of the prosthesis 32 from the left as shown in FIG. 23 until surface 116 of the pin 112 engages surface 50 of the prosthesis 32. Engaging rod 110 of the lapping tool 102 is then inserted from the right as shown in FIG. 23 until the rod 110 engages internal bore 114 of the pin 112 and surface 120 engages bottom surface 98 of the prosthesis 32. The shank 106 sized, as desired, to engage either the cylindrically shaped recess 82 or a recess with hexagonal surfaces 60. Shank 108 is then connected to a torque source which causes the deburring flange 104 to rotate and engaging surface 120 with paste 118 to polish bottom surface 98. As bottom surface 98 is polished, downwardly extending surface 57 is machined away in order to provide a polished bottom surface 98. Surface 122 of shank 106 will come into contact with bottom surface 124 of the recess 82 to limit the amount of polishing that will take place.

Figure 21:
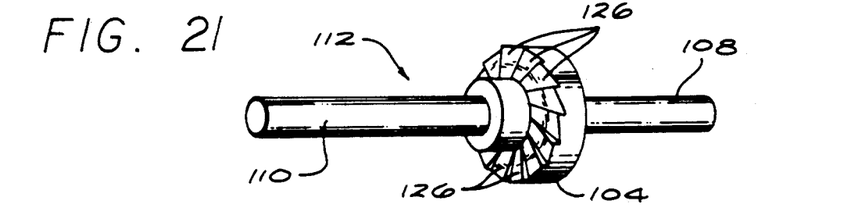
FIG. 21 is a perspective view of another embodiment of the lapping tool having cutting edges used to deburr or polish the bottom surface of the prosthesis of FIG. 4.

FIG. 21 shows another embodiment of the lapping tool 112 having cutting edges 126 on flange 104 that may be used to lap or deburr bottom surface 98. Milling paste 118 is not needed for such a tool 112.

Figure 28:
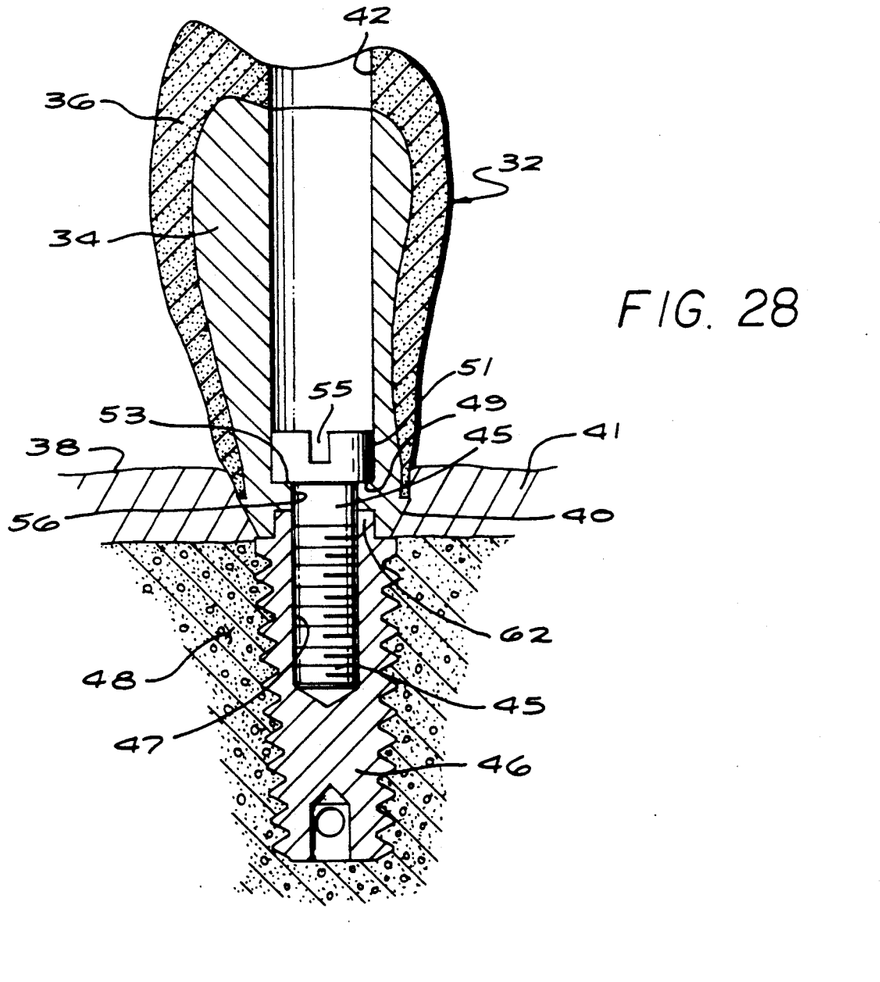
FIG. 28 is a partial cross-sectional view of the retrievable dental prosthesis of FIG. 2 taken similar to FIG. 4 showing how the prosthesis is directly connected by a slotted, flat-headed titanium alloy screw to the implant placed in a patient's bone structure.

FIG. 28 shows another embodiment of the retrievable dental prosthesis 32 of the present invention using a flat-headed titanium alloy screw 45 to connect the prosthesis 32 to the implant 46. The screw 45 has a flat annular-shaped surface 49 at the bottom of its head 51. Surface 49 bears against corresponding flat annular-shaped surface 53 at the bottom of cylindrically-shaped bore 42. Head 51 has a slot 55 that may be used to loosen or tighten the screw 45. All other features of the embodiment shown in FIG. 29 are similar to those of the embodiment shown in FIG. 4 except for the use of a flat-headed screw 45 instead of a screw 44 with a frustro-conically-shaped surface 50 at the bottom of its head 52.

Figure 29:
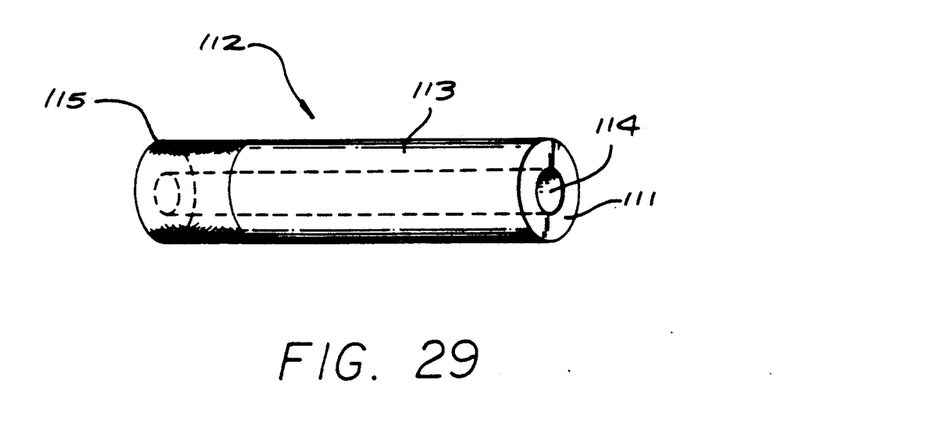
FIG. 29 is a perspective view of another embodiment of the guide pin having a flat end used with the lapping tool of FIG. 19 to polish the bottom surface of the prosthesis of FIG. 4.

Another embodiment of the guide pin 112 is shown in FIG. 29. This pin 112 is used with lapping tool 102 to polish the embodiment of the prosthesis 32 shown in FIG. 28. The pin 112 has an external cylindrical surface with a diameter 113 and a gripping surface 115. When the guide pin 112 and lapping tool 102 are used together (see FIG. 23), flat end 111 contacts annular-shaped surface 53 at the bottom of bore 42 and rod 110 of the lapping tool 102 engages internal bore 114 of the guide pin 112. Polishing is then performed as explained above.

A finished prosthesis 32 is shown in FIG. 24 having a porcelain layer 36 fused to the cast metal 34 using conventional techniques. The porcelain layer 36 preferably extends down the prosthesis 32 and stops at ledge 43 just above collar 40 which reinforces the base of the prosthesis 32. The prosthesis 32 may be fabricated without a porcelain layer 36. For example, resin may be used instead of porcelain, or the cast metal 34 may be used without any layer or coating.

After the prosthesis 32 is attached to an implant 46 in a patient's mouth by the installation tool 68, the access aperture 72 (see FIG. 9) is filled using conventional dental techniques. If any problems develop or regular maintenance or inspection is required, the filling may be removed and the installation tool 68 may be used to remove the prosthesis 32 by unscrewing screw 44. After treatment is completed, the prosthesis 32 may be reconnected back to the implant 46 and the access aperture 72 refilled with a suitable dental filling material.

Figure 25:
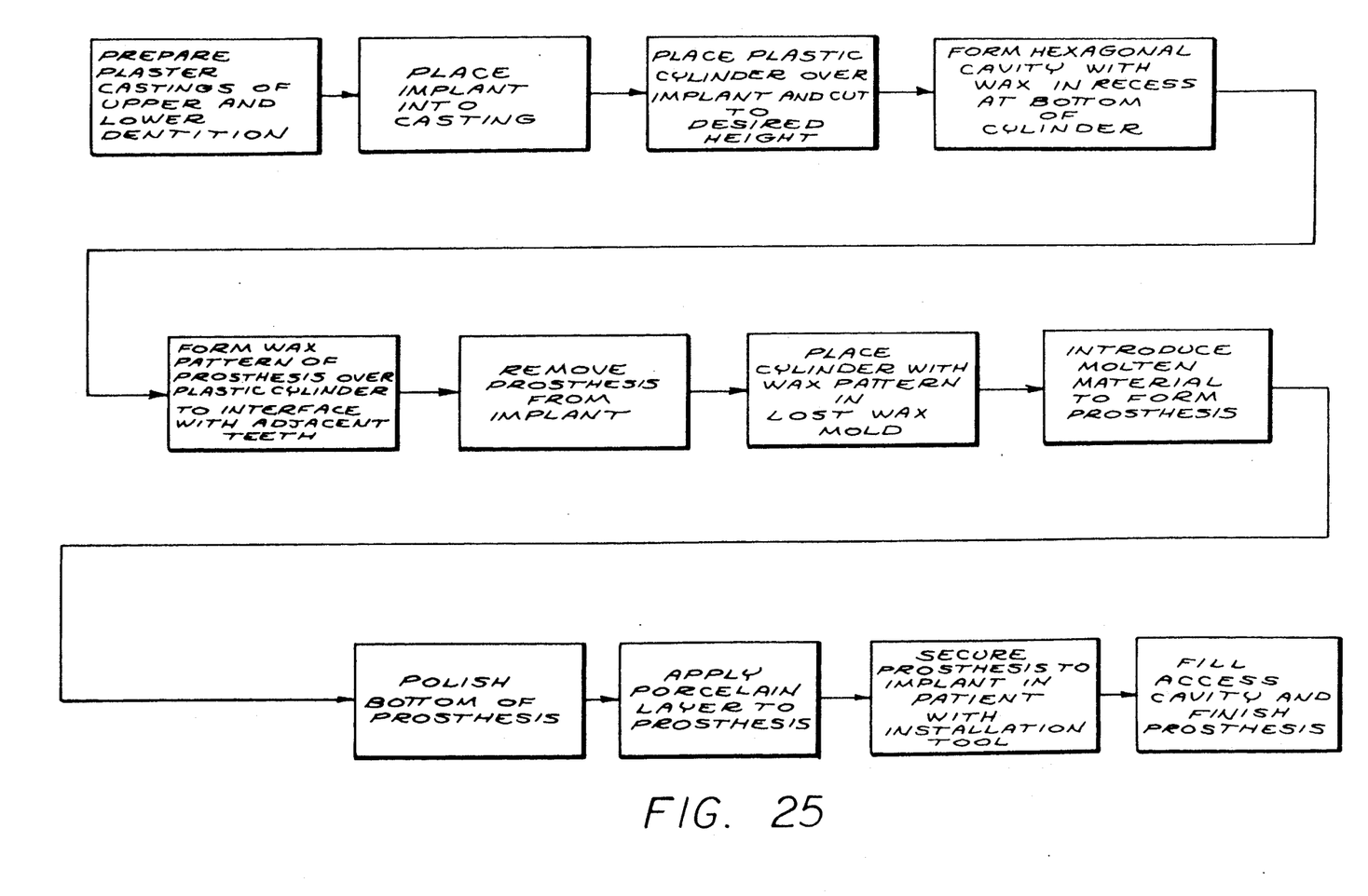
FIG. 25 is a flow diagram in block form illustrating the principles of the method of fabrication of the prosthesis of FIG. 4.

FIG. 25 is a flow diagram showing the various steps used to fabricate the prosthesis 32 of the present invention. Steps may be bypassed as desired to vary the design of the prosthesis. For example, the prosthesis 32 may be fabricated without hexagonal surfaces 60 at its base, or a porcelain layer 36 may not be used, or another type of layer may be used.

Two prostheses 32 may be joined together as shown in FIG. 26 by first using material to join the prostheses 32 together in a patient's mouth, such as inlay pattern resin like that sold under the trademark DURALAY by Reliance Dental Manufacturing Company, Worth, Ill. The two prostheses 32 are then removed from the patient's mouth and soldered together using a desirable dental alloy 138.

Figure 27:
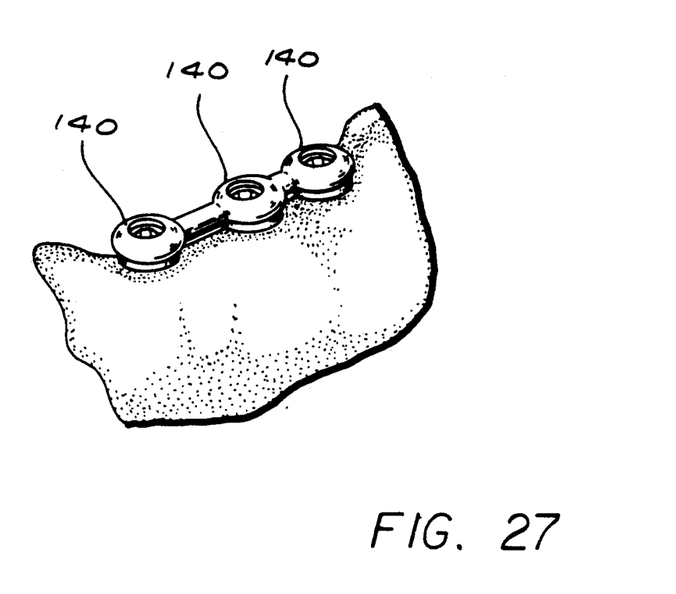
FIG. 27 is a perspective view of another embodiment showing a substructure for an overlay denture illustrating the principles of the present invention.

"Prosthesis" as used herein is intended to include, by way of example only and not limitation, any substructures or other dental structures used in conjunction with dental implants. For example, the present invention may also be used to form a substructure 140 such as shown in FIG. 27 for an overlay denture (not shown). The same lost-wax casting procedures described above may be used to fabricate the substructure. The overlay denture slips onto the underlying substructure 140 for retention. The substructure 140 offers lateral and vertical support for the overlay denture.

The above description discloses the preferred embodiments of the present invention. However, persons of ordinary skill in the art are capable of numerous modifications once taught these principles. Accordingly, it will be understood by those skilled in the art that changes in form and details may be made to the above-described embodiments without departing from the spirit and scope of the invention.

We claim:

1. A retrievable dental prosthesis adapted to be removably connected by a screw to an implant anchor, said implant anchor adapted to be embedded in a patient's dental bone structure and to be disposed below a top surface of said patient's overlying gingiva, said dental prosthesis comprising an integral cast metal portion removably connected to said implant anchor, said cast metal portion being shaped to generally represent contours of a tooth of said patient to be replaced by said prosthesis, said cast metal portion having a base with an annular bottom surface and means at said base for engaging said implant and interlocking therewith in order to prevent rotation of said cast metal portion with respect to said implant anchor, said cast metal portion having an access aperture passing therethrough from an upper position above said base downward toward said base, said screw being disposed inside and at a bottom of said aperture in order to removably connect said cast metal portion to said implant anchor so that said top surface of said patient's overlying gingiva and directly interfaces with said implant anchor, and so that said base interlocks with said implant anchor below said top surface of said gingiva, said aperture providing access to said screw so that said screw is capable of being selectively (a) loosened in order to remove said cast metal portion from said implant, and (b) tightened in order to removably connect said cast metal portion to said implant anchor.

2. The retrievable dental prosthesis of claim 1 wherein said engaging means includes internal mating surfaces in a recess in said base capable of engaging and interlocking with corresponding mating surfaces at an upward extension of said implant.

3. The retrievable dental prosthesis of claim 2 wherein said internal mating surfaces and said corresponding mating surfaces are hexagonal surfaces.

4. The retrievable dental prosthesis of claim 1 wherein said cast metal portion is contoured near said base to facilitate corresponding soft tissue health adjacent said base and to provide access for oral hygiene purposes.

5. The retrievable dental prosthesis of claim 1 wherein said cast metal portion is a dental alloy.

6. The retrievable dental prosthesis of claim 5 wherein said dental alloy is gold-palladium alloy.

7. The retrievable dental prosthesis of claim 5 wherein said dental alloy is 52% gold-palladium alloy.

8. A retrievable dental prosthesis adapted to be removably connected by a screw to an implant anchor, said implant anchor adapted to be embedded in a patient's dental bone structure and to be disposed below a top surface of said patient's overlying gingiva, said dental prosthesis comprising an integral cast metal portion removably connected to said implant anchor, said cast metal portion being shaped to generally represent contours of a tooth of said patient to be replaced by said prosthesis, said cast metal portion having a base and means at said base for engaging said implant anchor and interlocking therewith in order to prevent rotation of said cast metal portion with respect to said implant anchor, said cast metal portion having an access aperture passing therethrough from an upper position above said base downward toward said base, said screw being disposed inside and at a bottom of said aperture in order to removably connect said cast metal portion to said implant anchor so that said base extends downward below said top surface of said patient's overlying gingiva and is directly connected to and interlocked with said implant anchor below said top surface of said gingiva, said aperture providing access to said screw so that said screw is capable of being selectively (a) loosened in order to remove said cast metal portion from said implant, and (b) tightened in order to removably connect said cast metal portion to said implant anchor, said cast metal portion having an annular collar at said base, said collar having an annular ledge at the top thereof.

9. The retrievable dental prosthesis of claim 8 wherein said cast metal portion has a layer of porcelain fused to the outside surface thereof, said layer of porcelain extending downward to said ledge.

10. The retrievable dental prosthesis of claim 8 wherein said cast metal portion has a layer of resin at the outside surface thereof, said layer of resin extending downward to said ledge.

11. A retrievable dental prosthesis adapted to be removably connected to an implant anchor, said implant anchor adapted to be embedded in a patient's dental bone structure and to be disposed below a top surface of said patient's overlying gingiva, said dental prosthesis comprising a screw and an integral cast metal portion removably connected to said implant anchor by said screw, said cast metal portion being shaped to generally represent contours of a tooth of said patient to be replaced by said prosthesis, said case metal portion having a base with an annular bottom surface and means at said base for engaging said implant anchor and interlocking therewith in order to prevent rotation of said cast metal portion with respect to said implant anchor, said cast metal portion having an access aperture passing therethrough from an upper position above said base downward toward said base, said screw being disposed inside and at a bottom of said aperture in order to removably connect said cast metal portion to said implant anchor so that said annular bottom surface of said base extends downward below said top surface of said patient's overlying gingiva and directly interfaces with said implant anchor, and so that said base interlocks with said implant anchor below said top surface of said gingiva, said aperture providing access to said screw so that said screw is capable of being selectively (a) loosened in order to remove said cast metal portion from said implant, and (b) tightened in order to removably connect said cast metal portion to said implant anchor.

12. The retrievable dental prosthesis of claim 11 wherein said access aperture has a frustro-conically-shaped surface at said bottom thereof which engages a corresponding frustro-conically-shaped surface at the bottom of a head of said screw, said head having a recess therein with internal surfaces.

13. The retrievable dental prosthesis of claim 12 wherein said access aperture enters said cast metal portion so that said aperture provides access allowing an installation tool to engage said internal surfaces of said recess in said head in order to selectively loosen and to selectively tighten said screw.

14. The retrievable dental prosthesis of claim 11 wherein said access aperture has a flat annular-shaped surface at said bottom thereof which engages a corresponding flat annular-shaped surface at the bottom of a head of said screw, said head having a slot therein.

15. A retrievable dental prosthesis adapted to be removably connected to an implant anchor, said implant anchor adapted to be embedded in a patient's dental bone structure and to be disposed below a top surface of said patient's overlying gingiva, said dental prosthesis comprising a screw and an integral cast metal portion removably connected to said implant anchor by said screw, said cast metal portion being shaped to generally represent contours of a tooth of said patient to be replaced by said prosthesis, said cast metal portion having a base and means at said base for engaging said implant anchor and interlocking therewith in order to prevent rotation of said base metal portion with respect to said implant anchor, said cast metal portion having an access aperture passing therethrough from an upper position above said base downward toward said base, said screw being disposed inside and at a bottom of said aperture in order to removably connect said cast metal portion to said implant anchor so that said base extends downward below said top surface of said patient's overlying gingiva and is directly connected to and interlocked with said implant anchor below said top surface of said gingiva, said aperture providing access to said screw so that said screw is capable of being selectively (a) loosened in order to remove said cast metal portion from said implant, and (b) tightened in order to removably connect said cast metal portion to said implant anchor, said access aperture having a frusto-conically-shaped surface at said bottom thereof which engages a corresponding frusto-conically-shaped surface at the bottom of a head of said screw, said head having a recess therein with internal surfaces, said access aperture entering said cast metal portion from a back of said portion so that said aperture provides access allowing an installation tool to engage said internal surfaces of said screw in said head in order to selectively loosen and to selectively tighten said screw.

16. A retrievable dental prosthesis adapted to be removably connected to an implant anchor, said implant anchor adapted to be embedded in a patient's dental bone structure and to be disposed below a top surface of said patient's overlying gingiva, said dental prosthesis comprising a screw and an integral cast metal portion removably connected to said implant anchor by said screw, said cast metal portion being shaped to generally represent contours of a tooth of said patient to be replaced by said prosthesis, said cast metal portion having a base with an annular bottom surface, said cast metal portion having an access aperture passing therethrough from an upper position above said base downward toward said base, and a screw disposed inside and at a bottom of said aperture removably connecting said cast metal portion to said implant anchor so that said annular bottom surface of said base extends downward below said top surface of said patient's overlying gingiva and directly interfaces with said implant anchor below to said screw so that said screw is capable of being selectively (a) loosened in order to remove said cast metal portion from said implant, and (b) tightened in order to removably connected said cast metal portion to said implant.

17. A combination retrievable dental prosthesis and implant anchor comprising an implant anchor adapted to be embedded in a patient's dental bone structure and to be disposed below a top surface of said patient's overlying gingiva, an integral cast metal portion removably connected to said implant anchor, said cast metal portion being shaped to generally represent contours of a tooth of said patient to be replaced by said prosthesis, said cast metal portion having a base, an access aperture passing therethrough from an upper position above said base downward toward said base, and a connector disposed inside and at a bottom of said aperture removably connecting said cast metal portion to said implant anchor so that said base extends downward below said top surface of said patient's overlying gingiva and directly interfaces with said implant anchor below said top surface of said gingiva, said aperture providing access to said connector so that said connector is capable of being selectively (a) loosened in order to remove said cast metal portion form said implant, and (b) tightened in order to removably connect said cast metal portion to said implant.

18. A cylinder apparatus used for fabricating a cast metal dental prosthesis comprising an elongated cylindrically-shaped member having a first bore passing longitudinally therethrough, said first bore having a frustro-conically-shaped surface at the bottom thereof, said member having a cylindrically-shaped recess at a bottom thereof and a second bore therein having a smaller diameter than said first bore connecting said first bore to said recess, said member having an annular collar at said bottom thereof and a portion extending downward from said collar, said collar having an annular ledge at a top thereof, said member being made out of a material capable of being used for lost-wax casting procedures.

19. The cylinder of claim 18 wherein said material is a plastic material.

20. Milling apparatus used for deburring a cast metal dental prosthesis comprising:
a lapping tool having a shank with a deburring flange attached thereto, a shaft connected to said flange and an engaging rod connected to said shank, said shank capable of rotatably engaging a recess in a base of said cast metal prosthesis so that said deburring flange engages a bottom surface at said base of said prosthesis; and
a generally cylindrically-shaped elongated guide pin having an internal bore passing longitudinally therethrough, said guide pin capable of engaging an internal bore in said cast metal prosthesis so that one end of said guide pin engages a bottom of said bore in said prosthesis while said engaging rod of said lapping tool rotatably engages said internal bore in said guide pin in order that said deburring flange is capable of rotating and polishing said bottom surface of said prosthesis.

21. The milling apparatus of claim 20 wherein said deburring flange has cutting edges thereon.

22. The milling apparatus of claim 20 wherein said guide pin has a frustro-conically-shaped surface at said one end.

23. The milling apparatus of claim 20 wherein said one end of said guide pin is a flat end.

24. A method of fabricating a cast metal dental prosthesis comprising the steps of:
placing an implant in a master cast so that external surfaces of an upward extension of said implant are properly oriented to match orientation of said surfaces when said implant is placed in a patient's dental bone structure;
placing a plastic cylinder on top of said implant;
shaping a wax pattern over said plastic cylinder to generally represent contours of a tooth to be replaced by said prosthesis;
removing said cylinder with said wax pattern from said implant; and
casting a cast metal prosthesis using said cylinder with said wax pattern and lost-wax casting procedures.

25. The method of claim 24 further comprising the step of shaping wax in a recess in a bottom of said plastic cylinder before shaping said wax pattern in order to form internal surfaces that are capable of mating with said external surfaces of said implant.

26. The method of claim 24 further comprising the step of polishing a bottom surface of said cast metal prosthesis.

27. The method of claim 24 further comprising the step of fusing a porcelain layer to an outside surface of said cast metal prosthesis.

28. The method of claim 24 further comprising the step of applying a resin layer to an outside surface of said cast metal prosthesis.

29. The method of claim 24 wherein said cast metal prosthesis is made out of gold-palladium alloy.

30. The method of claim 24 further comprising the step of cutting a top portion off said plastic cylinder before shaping said wax pattern so that said cylinder is sized to represent the height of said tooth to be replaced.

31. The method of claim 24 wherein said cast metal prosthesis has an annular collar at the base metal prosthesis has an annular collar at the base thereof.

32. The method of claim 24 wherein said plastic cylinder has internal surfaces formed integrally in a recess in a bottom of said plastic cylinder, said internal surfaces capable of mating with said external surfaces of said implant.

33. A combination retrievable dental prosthesis and implant anchor comprising an implant anchor adapted to be embedded in a patient's dental bone structure and to be disposed below a top surface of said patient's overlying gingiva, an integral cast metal portion removably connected to said implant anchor, said cast metal portion being shaped to generally represent contours of a tooth of said patient to be replaced by said prosthesis, said cast metal portion having a base with an annular bottom surface and means at said base for engaging said implant anchor and interlocking therewith in order to prevent rotation of said base metal portion with respect to said implant anchor, said cast metal portion having an access aperture passing therethrough from an upper position above said base downward toward said base, and a screw disposed inside and at a bottom of said aperture removably connecting said cast metal portion to said implant anchor so that said annular bottom surface of said base extends downward below said top surface of said patient's overlying gingiva and directly interfaces with said implant anchor below said top surface of said gingiva, said aperture providing access to said screw so that said screw is capable of being selectively (a) loosened in order to remove said cast metal portion from said implant, and (b) tightened in order to removably connect said cast metal portion to said implant anchor.

34. A method of installing a dental prosthesis in a patient's jawbone, said jawbone having a predrilled bore therein, said dental prosthesis having an aperture therein and a base, said method comprising the steps of:
    installing an implant anchor in said predrilled bore formed in said jawbone below a top surface of said patient's overlying gingiva;
    mounting a dental prosthesis directly on top of said implant anchor so that said base of said prosthesis extends downward below said top surface of said patient's overlying gingiva and directly interfaces with said implant anchor below said top surface of said gingiva, said dental prosthesis comprising an integral cast metal portion shaped to generally represent contours of a tooth of said patient to be replaced by said prosthesis; and
    removably connecting said dental prosthesis to said implant anchor with a screw placed into said aperture in said dental prosthesis and threaded into said implant anchor.

35. The method of claim 34 wherein said mounting step includes engaging and interlocking said base of said dental prosthesis to said implant anchor so that said dental prosthesis is prevented from rotating with respect to said implant anchor.

36. The method of claim 35 wherein said base of said dental prosthesis has an annular bottom surface and said implant anchor has an annular top surface, said annular top and bottom surfaces directly interfacing with each other after said dental prosthesis is mounted onto said implant anchor.

37. A retrievable dental prosthesis adapted to be removably connected by a connector to an implant anchor, said implant anchor adapted to be embedded in a patient's dental bone structure and to be disposed below a top surface of said patient's overlying gingiva, said dental prosthesis comprising an integral portion removably connected to said implant anchor, said integral portion being shaped to generally represent contours of a tooth of said patient to be replaced by said prosthesis, said integral portion having a base and an access aperture passing therethrough from an upper position above said base downward toward said base, said connector being disposed inside said aperture removably connecting said integral portion to said implant anchor so that said base extends downward below said top surface of said patient's overlying gingiva and directly interfaces with said implant anchor below said top surface of said gingiva, said aperture providing access to said connector so that said connector is capable of being selectively (a) loosened in order to remove said integral portion from said implant, and (b) tightened in order to removably connect said integral portion to said implant.

* * * * *